(12) United States Patent
Caldara et al.

(10) Patent No.: US 11,324,971 B2
(45) Date of Patent: May 10, 2022

(54) IMPROVING SAFETY AROUND A LINEAR ACCELERATOR

(71) Applicant: ADAM S.A., Meyrin (CH)

(72) Inventors: Michele Caldara, Geneva (CH); Matevz Cerv, Geneva (CH); Roland Moser, Meyrin (CH); Hannes Pavetits, Soral (CH); Katarzyna Stachyra, Sergy (FR); Marina Giunta, Gex (FR)

(73) Assignee: ADAM S.A., Meyrin (CH)

( * ) Notice: Subject to any disclaimer, the term of this patent is extended or adjusted under 35 U.S.C. 154(b) by 54 days.

(21) Appl. No.: 16/982,010

(22) PCT Filed: Mar. 20, 2019

(86) PCT No.: PCT/EP2019/056939
§ 371 (c)(1),
(2) Date: Sep. 17, 2020

(87) PCT Pub. No.: WO2019/180069
PCT Pub. Date: Sep. 26, 2019

(65) Prior Publication Data
US 2021/0128949 A1    May 6, 2021

(30) Foreign Application Priority Data
Mar. 20, 2018   (EP) ..................... 18162858

(51) Int. Cl.
*A61N 5/10*   (2006.01)
*G01T 1/29*   (2006.01)
(Continued)

(52) U.S. Cl.
CPC .............. *A61N 5/1067* (2013.01); *G01T 1/29* (2013.01); *H05H 7/22* (2013.01); *H05H 9/044* (2013.01);
(Continued)

(58) Field of Classification Search
CPC ................... A61N 5/1067; A61N 2005/1087; G01T 1/29; H05H 7/22; H05H 9/044;
(Continued)

(56) References Cited

U.S. PATENT DOCUMENTS 5,440,210 A     8/1995  Bogaty et al.
5,714,875 A *   2/1998  Lawrence ................. G21F 1/08
                                                         324/71.3
(Continued)

FOREIGN PATENT DOCUMENTS

CN        105572452 A  *  5/2016
JP        H07263197 A  * 10/1995
(Continued)

OTHER PUBLICATIONS

Lee et al., The Beam Diagnostics System in the J-PARC LINAC; Proceedings of LINAC 2004; Lübeck, Germany, Apr. 1, 2005 (Apr. 1, 2005), pp. 441-443.
(Continued)

*Primary Examiner* — Marcus H Taningco
(74) *Attorney, Agent, or Firm* — Studebaker & Brackett PC (57) ABSTRACT

A linear accelerator system comprising a source arranged to produce a pulsed beam of charged particles, a linear accelerator string arranged to accelerate the pulsed beam up to a predetermined range of energies, and a pre-acceleration stage interposed between the source and the linear accelerator string and arranged to accelerate the pulsed beam up to an energy suitable for beam insertion into the linear accelerator string and perform bunching of the pulsed beam. An average current detector is arranged to measure an average current in the pulsed beam, the average current detector comprising at least one non-interceptive sensor placed at an input side of the linear accelerator string, downstream of the pre-acceleration stage, the sensor being responsive to the pulsed beam passing thereby.

14 Claims, 7 Drawing Sheets

(51) Int. Cl.
  *H05H 7/22* (2006.01)
  *H05H 9/04* (2006.01)
  *H05H 7/00* (2006.01)

(52) U.S. Cl.
  CPC ............... *A61N 2005/1087* (2013.01); *H05H 2007/008* (2013.01); *H05H 2277/113* (2013.01)

(58) Field of Classification Search
  CPC ....... H05H 2007/008; H05H 2277/113; H05H 9/041; H05H 9/00
  See application file for complete search history.

(56) References Cited

U.S. PATENT DOCUMENTS

| | | | | |
|---|---|---|---|---|
| 2004/0069958 A1* | 4/2004 | Dahl | ..................... | H05H 7/04 250/492.3 |
| 2015/0076350 A1* | 3/2015 | Plettner | ................ | H01J 37/244 250/336.1 |
| 2020/0069968 A1* | 3/2020 | Kobashi | ............... | A61N 5/1038 |

FOREIGN PATENT DOCUMENTS

| | | | | |
|---|---|---|---|---|
| JP | 2921433 B2 | * | 7/1999 | |
| JP | 2006079911 A | * | 3/2006 | ............. B82Y 40/00 |

OTHER PUBLICATIONS

Miura et al., Interlock of Beam Loss at Low-Energy Part of J-PARC LINAC, Nuclear Instruments & Methods in Physics Research, Section A, vol. 408, Jan. 1, 2016 (Jan. 1, 2016), pp. 405-408.
Sato et al., Upgrade of Beam Diagnostics in LEBT and MEBT of J-PARC LINAC, Proceedings of LINAC 2006, Knoxville, Tennessee, US, Aug. 1, 2008 (Aug. 1, 2008), pp. 268-270.
Peters et al., Beam Diagnostics for the Heavy Ion Cancer Therapy Facility, AIP Conference Proceed, American Institute of Physics, New York, US, No. 546, May 8, 2000 (May 8, 2000), pp. 519-526.
Sieber et al., Beam Diagnostics Layout for the Fair Proton LINAC, Proceedings of the LINAC 2014, Geneva, Switzerland, Dec. 1, 2014 (Dec. 1, 2014), pp. 998-1000.
International Search Report issued in PCT/EP2019/056939; dated May 24, 2019.
International Preliminary Report on Patentability and Written Opinion issued in PCT/EP2019/056939; dated Sep. 22, 2020.

* cited by examiner

IMPROVING SAFETY AROUND A LINEAR ACCELERATOR

BACKGROUND OF THE INVENTION

The present invention relates generally to linear accelerators. Linear accelerators may be used in radiotherapy, in industry, in research or in academic institutions.

Linear accelerators are used in radiotherapy to accelerate particles, typically electrons or protons, up to energies sufficient to allow them to travel to a depth in tissue to irradiate and impart energy to a tumor. In the case of electrons they may alternatively be directed onto a target of material of large atomic number to create high energy X-rays which themselves are then used to treat a tumor at depth.

Typically particles are generated in a source (for example an Electron Cyclotron Resonance Ion Source (ECRIS) or ion plasma source for protons, an electron gun for electrons) and injected into a linear accelerator complex where they are accelerated by high frequency radiofrequency (RF) fields up to a required energy or energies. Acceleration typically proceeds in stages. The production of a high energy output beam, suitable for radiotherapy treatment or other use, in practice may involve several accelerator sub-units, possibly as many as 10-14, each comprising a sequence of individual accelerator cavities connected to waveguides arranged to couple in the driving RF fields. The RF fields are typically produced by klystrons or magnetrons.

In one linear accelerator solution a proton beam is formed into pulses in a proton source injector assembly and these are introduced into a pre-accelerator stage, typically a Radiofrequency Quadrupole (or RFQ) which accelerates the initially drifting pulses up to 5 MeV. During this process of pre-acceleration the pulses gain a bunched structure at 750 MHz as the protons in the pulse start to interact with the accelerating RF field. At the output of the RFQ each pulse is fed into the input of a first linear accelerator stage as a bunched pulse, for eventual acceleration up to medically useful treatment energies. In a particular embodiment a chopper element is arranged to create the beam pulse in a proton source injector assembly. The chopper element, the pre-accelerator stage and the linear accelerator stages operate at a repetition rate of up to 200 Hz. In each subsequent linear accelerator stage applied RF fields couple to the bunches in each pulse and accelerate them to higher and higher energies, while maintaining the structure of the pulse.

The beam path from beginning to end of the accelerator complex may be many meters long and is typically shielded throughout its length.

A particle beam which interacts with matter, for example the walls of the accelerator cavity or any surrounding shielding or indeed the material of the surrounding room, is attenuated by the atomic structure of this surrounding material and creates a secondary particle shower.

The sum of this radiation escaping to the outside of the shielding is known to the skilled person as prompt radiation to the environment. The amount of prompt radiation is proportional to the beam energy and intensity. Further, in the case of a proton beam, nuclear interactions between the proton beam itself and material induces activation in the material. Activation is the process by which a material, under the action of a radiation source, for example in this case a proton beam, becomes itself radioactive. This potential for activation can pose a danger to personnel working in and around an accelerator. Additionally, the radiation produced by activation can be harmful to machinery and electronics. In particular the electronic and control systems of the linear accelerator itself should not be exposed to excessive radiation.

Typically, facilities that produce radiation must comply with local regulatory requirements, in particular in relation to radiation levels. In order to comply the environment must be monitored for excess radiation. Radiation monitors, however, typically have a long reaction time in the event of excess radiation produced.

Regulatory requirements concerning exposure to radiation vary across jurisdictions, but a typical regulatory requirement, concerning a linear accelerator arranged to accelerate a beam of protons and situated in a shielded concrete bunker, might be for the effective dose rate induced by stray radiation during the beam operation to be maintained below 0.5 µSv/h in accessible areas of the bunker, and 3 µSv/h in core areas of the bunker. The former rate could be defined as the allowable dose rate for a legally defined 'non-designated' or 'non-supervised' area, and the latter could be legally defined as the allowable dose rate for a 'designated' or 'supervised' area. Under these circumstances some form of radiation monitoring would be performed, either monitoring in the bunker spaces themselves or monitoring of individual staff members, for example using individual dose badges, in order to maintain the acquired dose rate below the threshold level.

The legal definitions of designated areas such as 'supervised area' and non-supervised area' may vary between jurisdictions and in some jurisdictions may vary depending on whether patients are allowed into the area or not.

However, radiation monitoring detectors placed in the bunker spaces typically provide a relatively slow environmental monitoring which is unsuitable for the purposes of protection. A typical rate of measurement is one measurement per minute, whereas a beam can be produced and accelerated many hundreds of thousands of times during this one minute, and in a worst case scenario each beam could produce dangerous levels of prompt radiation. Additionally they measure ionizing radiation at a specific point in space and therefore do not provide a detailed map of radiation levels surrounding the machine. In particular they may miss hotspots of prompt radiation. In general, radiation monitors may only detect severe violations of radiation protection regulations well beyond the limits for non-supervised areas.

Personnel dose badges typically suffer the disadvantage that they are only accessed and read out after dose has accrued. They are extremely suitable for monitoring personnel in areas where the average dose rate is well mapped and well understood, and are less well suited to protecting staff around equipment which may cause the creation of unpredictable prompt radiation.

In view of the above, a problem of the invention is to develop a measure for monitoring radiation in a linear accelerator system which removes, at least in part, the above mentioned drawbacks of the prior art.

SUMMARY OF THE INVENTION

Accordingly, the invention proposes a linear accelerator system comprising a source arranged to produce a pulsed beam of charged particles, a linear accelerator string arranged to accelerate the pulsed beam up to a predetermined range of energies, and a pre-acceleration stage interposed between the source and the linear accelerator string and arranged to accelerate the pulsed beam up to an energy suitable for beam insertion into the linear accelerator and perform bunching of the pulsed beam, wherein an average current detector is arranged to measure an average current in the pulsed beam, said average current detector comprising at least one non-interceptive sensor placed at an input side of the linear accelerator string, downstream of the pre-acceleration stage, said sensor being responsive to the pulsed beam passing thereby.

The invention derives from the observation that the level of radiation detectable outside an accelerator unit depends upon the beam current. These levels may vary from accelerator to accelerator. By maintaining the average beam current at or below a predetermined value the radiation outside the accelerator units may be maintained below a predictable value.

According to a preferred embodiment, the linear accelerator system further comprises an interlock device, wherein the average current detector is configured to provide a value of the measured average current in the pulsed beam, compare said value with an average current threshold, and if said value exceeds the average current threshold, control the interlock device to turn off the pulsed beam.

In a further embodiment an average current detector is arranged to measure an average current in the bunched beam pulse, said average current detector comprising at least one non-interceptive sensor placed at an input side of the linear accelerator string, downstream of the pre-acceleration stage, said sensor being responsive to the bunched beam pulse passing thereby. Accordingly, in a further preferred embodiment, the linear accelerator system further comprises an interlock device, wherein the average current detector is configured to provide a value of the measured average current in the bunched beam pulse, compare said value with an average current threshold, and if said value exceeds the average current threshold, control the interlock device to turn off the beam.

In this way it is ensured that prompt radiation levels never exceed a predetermined threshold.

The predetermined dose threshold for radiation levels is typically defined by legal regulation, however it may also be defined locally, to a defined level considered appropriate by a radiation protection expert.

The relationship between the average current of the beam and the radiation level which that beam produces may be determined empirically or experimentally or by modelling or simulations which may take into consideration any or all of the accelerator material and geometry, the specific size and material properties of individual accelerator cavities, and the surrounding environment including shielding, walls, and ancillary systems. The simulations may also take into consideration the maximum allowed dose rate outside the accelerator room.

By measuring average current at a point between the pre-accelerator and the linear accelerator stages and comparing the measurement to a threshold, and by using the comparison to trigger an interlock if the average current is too high, we are able to turn the machine off if beam conditions are created which would result in too high a quantity of prompt radiation or in activation of the linear accelerator and its surroundings.

In particular it is useful during commissioning or maintenance of a system in which personnel are constantly accessing the space around the machine while intermittently firing beams. The interlock can quickly turn the machine off, thus minimizing the probability of material activation.

In particular, in the early stages of acceleration of the beam, the process of turning the initially drifting proton pulses into accelerated pulses is not completely efficient and stray protons may drop out of the pulses, essentially be lost out of the pulses, as the pulses begin to accelerate. These stray protons which exist in the pre-accelerator, for example an RFQ, but which no longer form part of a coupled bunch, i.e. a bunch coupled to an accelerating field, cannot form part of the ultimately accelerated proton treatment beam. Yet until these stray protons are lost from the vacuum in the accelerator cavities (for example by absorption onto the internal cavity wall) they remain present as a moving charge in the accelerator cavity space and may be detected. The inventors have realized that using a fast detector to detect average current, for example by using a beam position monitor (BPM), this has the advantage that the stray protons which have been lost from the bunches are not detected. A fast detector, for example a BPM, only detects and measures the bunched part of the beam.

This allows for a better estimation of intensity of the fully accelerated beam and is efficient because any stray, non-bunched protons will not be picked up, coupled to and accelerated further by the coupling RF fields and will therefore not be part of the accelerated beam which contributes to radiation dose.

In other words by using a fast detector, for example a BPM, to measure average current it is possible to detect only protons which will be capable of potentially contributing to either prompt radiation or activation or both. This provides an extremely efficient way of maintaining safe use of an accelerator system by triggering an interlock to turn it off when the average current through the accelerator exceeds a level likely to cause prompt radiation or activation, while also ensuring the interlock is not triggered unless the current measured is capable of being accelerated.

In a particular embodiment the use of a BPM offers the further advantage that a measurement can be made using components that are already placed between accelerating and pre-accelerating structures in order to control and detect the beam.

In a specific embodiment the space between the pre-accelerator and the linear accelerator stages, sometimes known as a Medium Energy Beam Transfer Line (MBTL or, alternatively, MEBT), comprises a slow beam current transformer, used to measure transmission along the RFQ;

a BPM, used to measure beam position for calibration of the beam so that it correctly enters the next linear accelerator stage;

steerers, typically electromagnets (EMs) used to change direction of the beam, in a particular embodiment there are two EMs, each of which arranged to act on the beam in both a nominal x-direction and an orthogonal y-direction, in a further typical embodiment the steerers are set using the output of the BPM, which may be performed automatically or through an operator;

one or more permanent magnet quadrupoles (PMQs) to focus or defocus the beam, in a particular embodiment there are two PMQs; and a vacuum sector valve, to assist in creation and maintenance of the a vacuum along the beam line.

By measuring average current using a BPM which is positioned in the MEBT for other purposes, it is possible to create a safety measurement which does not require the provision or placement of further detectors along the beamline and which, therefore, does not cause an increase in the total length of the accelerator system. In other words, by using an existing component to measure average current and then use average current to trip an interlock in dependence on a threshold value, we avoid the insertion or inclusion of an additional component along the beamline, while also ensuring a reduced footprint for the overall system.

Therefore by using an existing BPM to detect average current a safety measurement can be achieved without the addition of extra bulky and MBTL- or MEBT-lengthening components.

The measurement of average current can be taken using any appropriate fast detector, which in practice is a capacitive detector sensitive to the bunched structure of the beam (at 750 MHz). As an alternative to the BPM a phase probe can be used.

Further alternative embodiments with the same frequency response include the Fast Beam Current Transformer (FCT), Wall Current monitor or Resonant cavity BPM, however the FCT suffers poor beam intensity resolution and the wall current monitor and cavity BPM suffer complexity of system which make them difficult and expensive to use.

In particular the reading of average current detection can be taken using any BPM positioned along the beam line, but it offers particular advantages when the measurement is taken from the BPM positioned between a pre-accelerator and the first accelerating structure because this is the first point along the beam line where it is possible to detect protons which could theoretically contribute to prompt radiation and activation.

If the particle accelerator allows for high repetition rates of production of the pulsed beam, the threshold for the maximum allowed produced average current may be reached very swiftly. The feedback loop time from current detection to the interlock system must therefore be minimized to ensure a minimal effect of prompt radiation due to high intensity beam pulses. For pulses with the beam charge of the order of 100 pAs and trigger rates between 1 Hz and 200 Hz, the response time must be of the order of one second. The average current detector allows for an even faster actuation—of the order of tens of milliseconds after reaching the threshold—due to its specific implementation.

In an embodiment the detection rate is of the order of once per second and this allows the creation of a workable safety detector system which detects the potential for a dangerous situation with a much shorter time period than environmental radiation detectors in the art, and which turns off the beam to avoid such dangerous situations arising.

The average current detector (hereinafter, also ACD) therefore ensures that the radiation levels in the areas surrounding the accelerator, for every phase of its commissioning, or in clinical, academic or industrial use, are kept within limits by preventing the linear accelerator from producing excessive amounts of accelerated beam.

According to an advantageous embodiment, the average current detector comprises at least one further sensor, hereinafter second sensor, placed downstream of said sensor, hereinafter first sensor, along said linear accelerator string, and wherein the average current detector is configured to provide a value of difference between the average current measured at the first sensor and the average current measured at the second sensor.

In this way, the average current detector can be used to detect beam losses. If multiple sensors are placed along the beam line at intervals throughout the linear accelerator they can be used to determine, in the event of beam loss, for example due to a failure of RF-cavity coupling, where in the accelerator beam loss has occurred and the magnitude of the loss.

The reaction time of the system is typically in the order of milliseconds.

At least one sensor of the average current detector is placed at the entrance or input to the linear accelerator, and this ensures that beam current can be monitored for excess over the predetermined threshold before it is accelerated along the accelerator. In other words, placement of the ACD at an accelerator input ensures that the beam is switched off before surrounding dose achieves potentially dangerous levels. An additional advantage is that in the event of a beam loss along the accelerator, by placing the ACD at an input to the accelerator it is able to monitor the current of the accelerated beam before the beam is lost. Even a beam which is subsequently lost may produce dangerous levels of prompt radiation, if the beam current is too high, during its partial passage through the accelerator.

The invention therefore reduces the probability that personnel and machine are exposed to radiation and/or material activation. It also allows accelerator radiation shielding to be designed without an excessive margin. This provides economic savings because the shielding for a particle linear accelerator has a considerable deleterious economic impact on the construction of linear accelerator housings and buildings, for example particle therapy centers. Thus the average current detector also has the advantage that it may minimize building costs.

In an embodiment the average current detector triggers an interlock, disabling the beam, if the measured beam current exceeds a predefined threshold. In a further embodiment the threshold is hard-coded in the system which prevents the threshold from being accidentally changed during operation. A quick response can be achieved by implementing the signal processing in real-time digital signal processing hardware, for example a Field Programmable Gate Array (FPGA), thus ensuring a faster shutdown of the beam.

BRIEF DESCRIPTION OF THE DRAWINGS

Some preferred, but non-limiting, embodiments of the invention will now be described, with reference to the attached drawings, in which.

DETAILED DESCRIPTION

Figure 1:
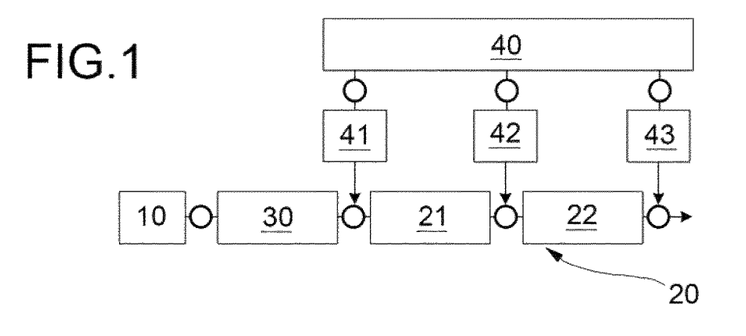
FIG. 1 shows the layout of an initial portion of a linear accelerator system.
Figure 2:
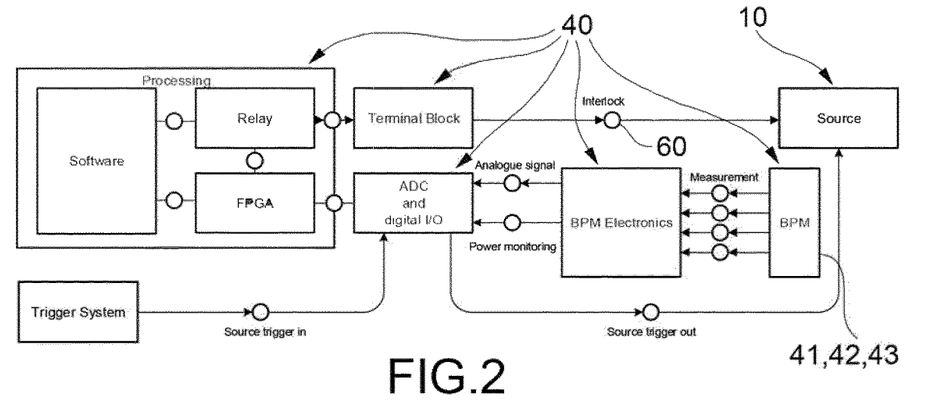
FIG. 2 shows the layout of a prototype system with an average current detector, showing the interfaces of the detector to other components.

With reference to FIG. 1, an exemplary proton radiotherapy system comprises a proton source 10 arranged to produce a pulsed beam of protons, and a linear accelerator string 20 arranged to accelerate the pulsed beam up to a range of energies suitable for treatment, up to a maximum of, for example, 250 MeV.

The acceleration is achieved in stages which include a first pre-acceleration stage or buncher 30 in which the pulsed beam is accelerated up to an energy suitable for beam insertion into the first accelerating structure of the linear accelerator string 20. The pre-accelerating stage 30 may also perform bunching of the pulses.

In a particular embodiment the pre-accelerator stage is a radiofrequency quadrupole (RFQ). In a specific embodiment the beam at the input of the RFQ may be a 5-microsecond-long pulse of continuous beam. Within this 5 μs window the particles may be spread uniformly. In the RFQ the particles are either slowed down or speeded up by the action of electromagnetic fields and in doing so form packets or bunches. Typically these are a few cm apart from one another. The beam therefore emerges from the RFQ in pulses which comprise bunching. The RF fields applied to the subsequent accelerator cavities must be synchronized to couple to these bunches.

Any particles outside these coupled packets (either trailing or leading) will not be accelerated further and will be lost from the beam. However, even if they are subsequently lost from the beam at some point along the line of accelerator cavities they may still contribute to excessive prompt radiation.

An average current detector 40 (hereinafter, also indicated as ACD) is arranged to measure an average current in the pulsed beam. The average current detector 40 comprises at least one non-interceptive sensor placed at an input side of the linear accelerator string 20, downstream of the pre-acceleration stage 30, said sensor being responsive to the bunched beam pulse passing thereby. In the example shown in FIG. 1, there is a first sensor 41 placed between the pre-acceleration stage 30 and a first linear accelerator component 21 of the linear accelerator string 20, a second sensor 42 placed between the first linear accelerator component 21 and a second linear accelerator component 22, and a third sensor 43 placed between the second linear accelerator component 22 and the remaining components of the linear accelerator string (not shown). A conventional linear accelerator string for radiotherapy purposes generally comprises between 10 and 14 linear accelerator components.

In a specific embodiment the first accelerator component 21 is a side coupled drift tube linear accelerator (SCDTL).

In a specific embodiment the beam pulse duration is in the order of microseconds, whilst the bunch duration is in the order of fractions of nanoseconds, so inside the linear accelerator components each beam pulse comprises some hundreds of bunches, repeated at the field frequency of the RFQ, or pre-accelerator 30. In a specific embodiment this may be at 750 MHz, giving a bunch period of 1.3 ns.

In practice approximately 70% of the beam is lost inside the RFQ 30 during this packaging into bunches. These lost particles are not relevant, or important, because they are not accelerated to a sufficiently high energy to cause the production of prompt radiation.

It is the bunched beam at the output of the RFQ 30 which is accelerated further and becomes a potential radiation hazard.

In a particular embodiment the average current detector performs non-interceptive continuous monitoring of the average beam current. In a specific embodiment this is performed on the beam accelerated above a certain energy, for example above or equal to 5 MeV/u which may be for example the energy of the pulsed beam found at the output of a radiation source or pre-accelerator. The effect of this monitoring, in combination with the interlock, is to maintain the effective dose rate produced by the stray radiation during the beam operation to below 0.5 μSv/h in a specific embodiment, depending on the specific structure and arrangement of the accelerator and the specific structure of the surrounding space. In a particular embodiment 0.5 μSv/h may be the limit for a non-supervised area in the accessible areas outside an accelerator room.

In a particular embodiment a suitable threshold value for average current may be 6 nA when the accelerator is arranged to accelerate a beam up to a maximum energy of 80 MeV/u.

In particular it has been found that an average beam current of up to maximum 6 nA allows safe prompt radiation levels outside the bunker if the losses along the accelerator are limited to 10% and the beam is properly dumped in the shielded MLFC, or beam dump, at 80 MeV. This may occur, for example, during commissioning of a linear accelerator intended for medical use. In this case the residual dose rate would be below the limit of Supervised Radiation Area after 1-hour cooling time even in case of 120-day irradiation period.

The average current detector of the invention is particularly useful when used in an accelerator placed inside a concrete bunker which is considered a radiation-controlled area but in which the concrete walls are insufficient to provide complete shielding for the maximum beam current, energy and repetition rate that could be generated by the accelerator.

The sensor(s) 41-43 of the average current detector may comprise a capacitive sensor, i.e. a pickup, which is a non-interceptive device that senses the electric field of the beam as it passes, and may comprise one or more electrodes. Possible alternatives for capacitive pickup include the Beam Position Monitor (BPM) with four electrodes, or, the Phase Probe with a single electrode, or, any non-destructive pickup, or, beam current transformers such as an AC current transformer (ACCT) or Fast current transformer (FCT).

Figure 4:
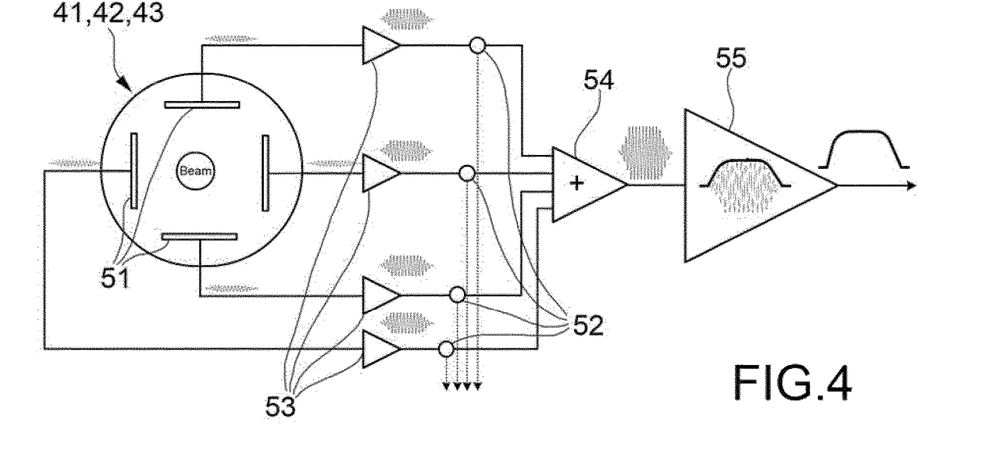
FIGS. 4 and 5 show the layout of a beam position monitor and the respective analogue electronic part.

In a specific embodiment the sensor(s) of the average current detector is(are) a BPM, as shown in FIG. 4.

Using a BPM for the sensor(s) 41-43 has the advantage that if space along the beam line is constricted then the signal from existing BPMs that may be used in a linear accelerator and inserted along the beam line for other monitoring purposes, may be used by splicing the output signal lines from these BPMs before the BPM readout. The average current detector can therefore be utilized in a manner in which the use of existing space is maximized, or in a manner in which no additional space is taken up. The invention therefore saves space while allowing monitoring of the beam to reduce staff exposure to radiation.

Figure 5:
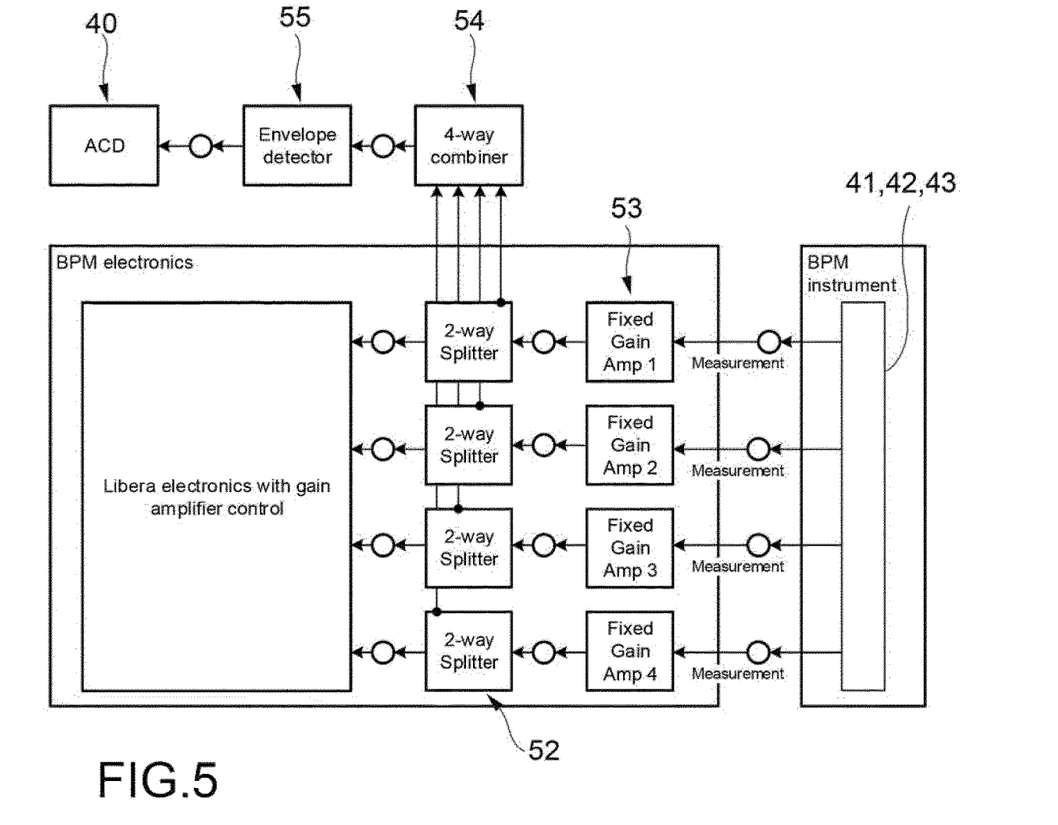

In an embodiment, signals from the four BPM electrodes 51 are first amplified at 53, typically with a fixed gain amplifier. Amplification is required because the signals, coming from non-interceptive pickups 51 are typically too weak to be directly split. After amplification they are split, at 52, so that the average current detector may run in parallel with the existing beam position monitoring system, as shown in FIG. 4 (the dashed lines show the connections to the readout of the BPM). The four signals are then recombined at 54 to remove the beam position dependence. After recombination an RF power detector 55 is used to detect the envelope of the beam pulse. The envelope signal is further buffered and digitized by a fast analogue to digital converter (ADC).

The digitized signal is processed in a Field-programmable gate array (FPGA), which allows for a deterministic algorithm execution.

Figure 3:
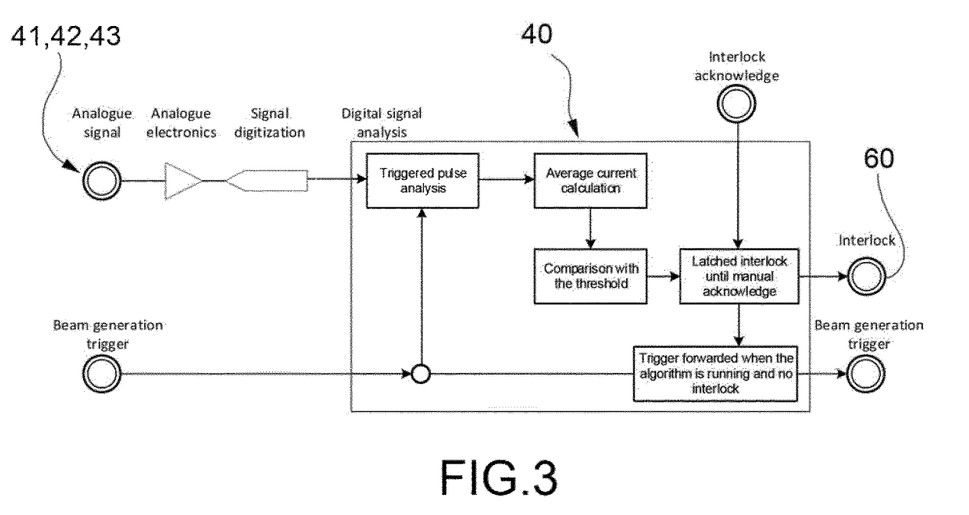
FIG. 3 shows the layout of a prototype architecture of the average current detector.

First, the signal analysis is carried out at every trigger for beam generation (see FIG. 3). This is to ensure that the signal is only analyzed when the accelerator is producing the beam, thus increasing the measurement accuracy of the system. To ensure that the measurement takes place at the actual beam trigger, the trigger line is routed from the generator to the ACD 40 and subsequently to the source 10. The beam is pulsed, inducing an electrical pulse with measurable parameters such as area, amplitude, width etc. The pulse area is directly proportional to the beam charge and must be pre-calibrated using an external beam instrument such as a Faraday Cup.

Second, the measured beam charge is accumulated, averaged and scaled to calculate the average current.

Third, the average current value is continuously compared to a hard-coded threshold. If it exceeds that threshold, it flags an alarm.

Finally, the alarm is latched and acts on a relay, issuing an interlock that may only be acknowledged (reset) manually. The latched alarm also inhibits the beam generation trigger output.

The interlock signal is connected to an interlock device 60 which, by switching off, prevents the accelerator from accelerating the beam. One example is the chopper magnet or dipole magnet (not shown) conventionally placed at the end of the proton source 10. When interlocked, it diverts the entire low-energy beam from the source into a beam dump. In an alternative embodiment the system is arranged to fail-safe and the beam is sent automatically into a beam dump unless diverted into the pre-accelerator, for example an RFQ. In this instance the interlock stops diversion of the beam into the pre-accelerator or RFQ.

The first BPM 41 only measures the beam that is bunched properly after the RF quadrupole (RFQ) (at 5 MeV/u). Given that the de-bunched part of the beam cannot be further accelerated in the following accelerating cavity, the inventors consider that it is sufficient to measure the bunched beam at the start of the accelerator (e.g. directly after the RFQ)—these measurements give a clear indication about the beam charge downstream of the measurement point.

When using only one BPM, its position along the accelerator is important. The assumption is that there are always some beam losses incurred along the accelerator. If the measurement took place at the end of the accelerator, it would not detect these losses and would therefore underestimate the radiation produced. This is avoided by placing the BPM close to the beam source (at the position where the beam is already bunched and has been accelerated to about minimum activation energy, which is few MeV for protons). Such configuration provides a reliable estimate of the radiation produced downstream in the worst-case scenario whereby the entire beam is lost, increasing the safety aspect of the system.

In an embodiment an ACD system may include a dynamic range of almost 40 dB, resolution of less than 1 µA, a bandwidth of more than 2 MHz, a reaction time of less than or equal to 5 ms, and be capable of detecting a current of the order of 100 nA.

In a further specific embodiment the ACD 40 allows for connecting additional BPMs mounted downstream to the same digital processing unit and to assign different thresholds for different beam energies.

Figure 6:
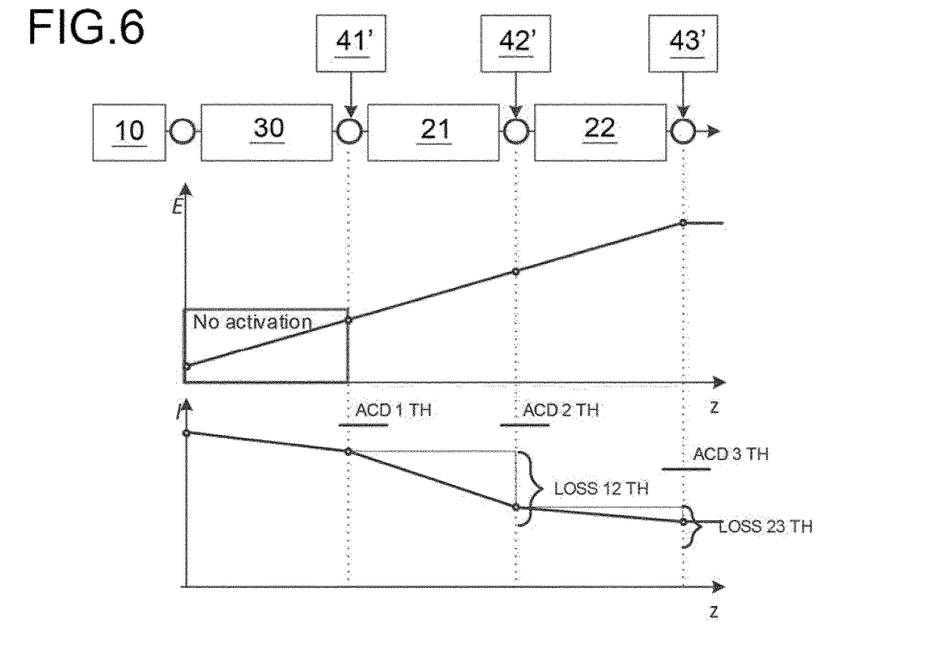
FIG. 6 shows a diagram representing the energy increase and the beam current decrease along the accelerator.
Figure 7:
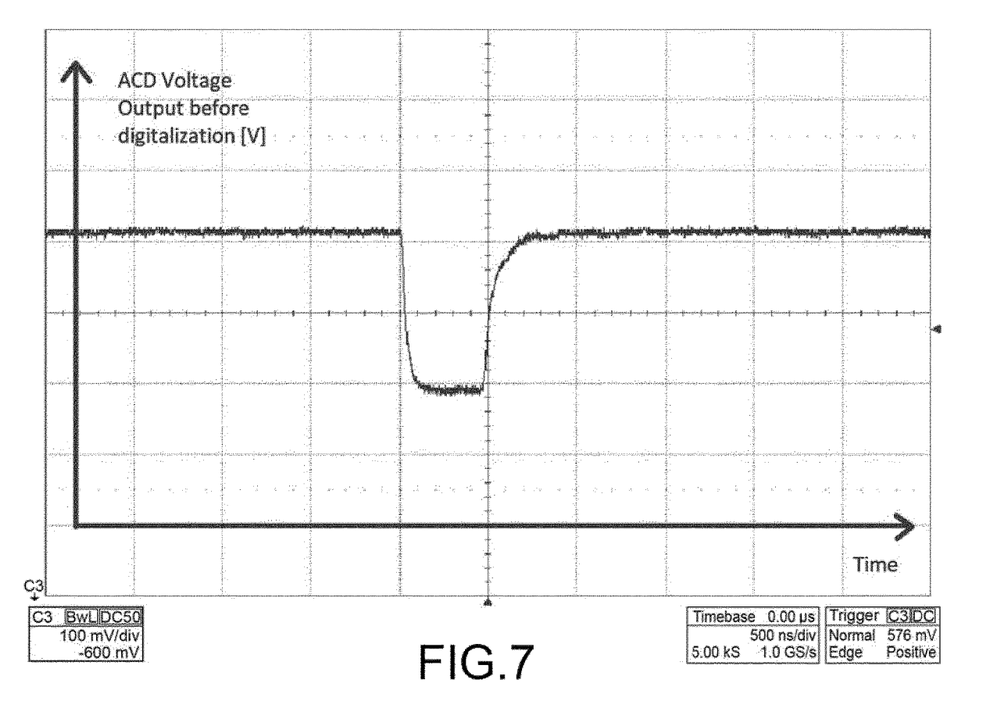
FIG. 7 shows an ACD signal at the output of an envelope detector for a 500 ns beam pulse.
Figure 8:
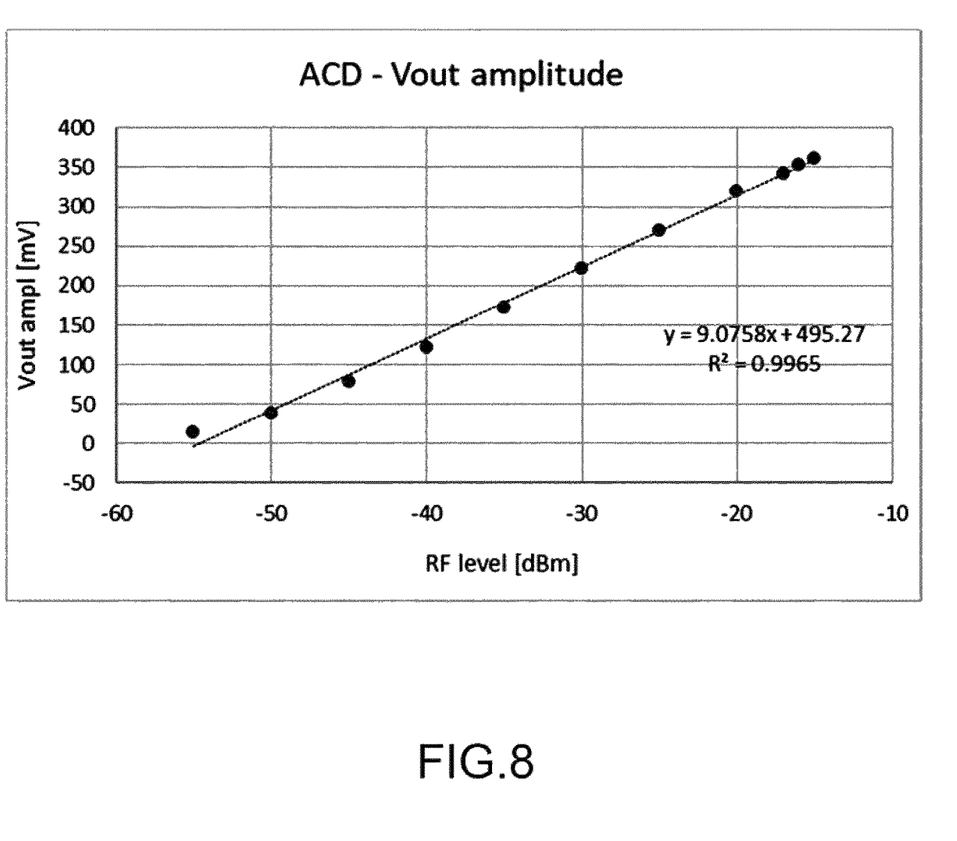
FIG. 8 shows the linear response of the average current detector to an injected RF pulse over a 40 dB dynamic range.

In addition, the values measured in the several BPMs may be compared to determine beam transmission loss (see FIG. 6)—it can therefore be determined how much beam has been lost between any two adjacent BPMs. The beam that is lost is inevitably producing stray radiation, therefore transmission loss gives us a good estimate of the radiation produced. A maximum average transmission loss per sector (LOSS 12 TH, LOSS 23 TH) can be added as a threshold to complement the average current thresholds (ACD 1 TH, ACD 2 TH, ACD 3 TH). This threshold is also derived from simulations and may vary for different energies. The transmission loss may therefore be used to discern between regular beam losses (continuous loss of beam along the accelerator) and incidental situations (RF breakdowns, magnet quenches, power electronics failures etc.). Finally, by limiting material activation, the machine cool-down time is reduced, which in turn minimizes intervention time during operation, maximizing machine uptime.

Figure 9:
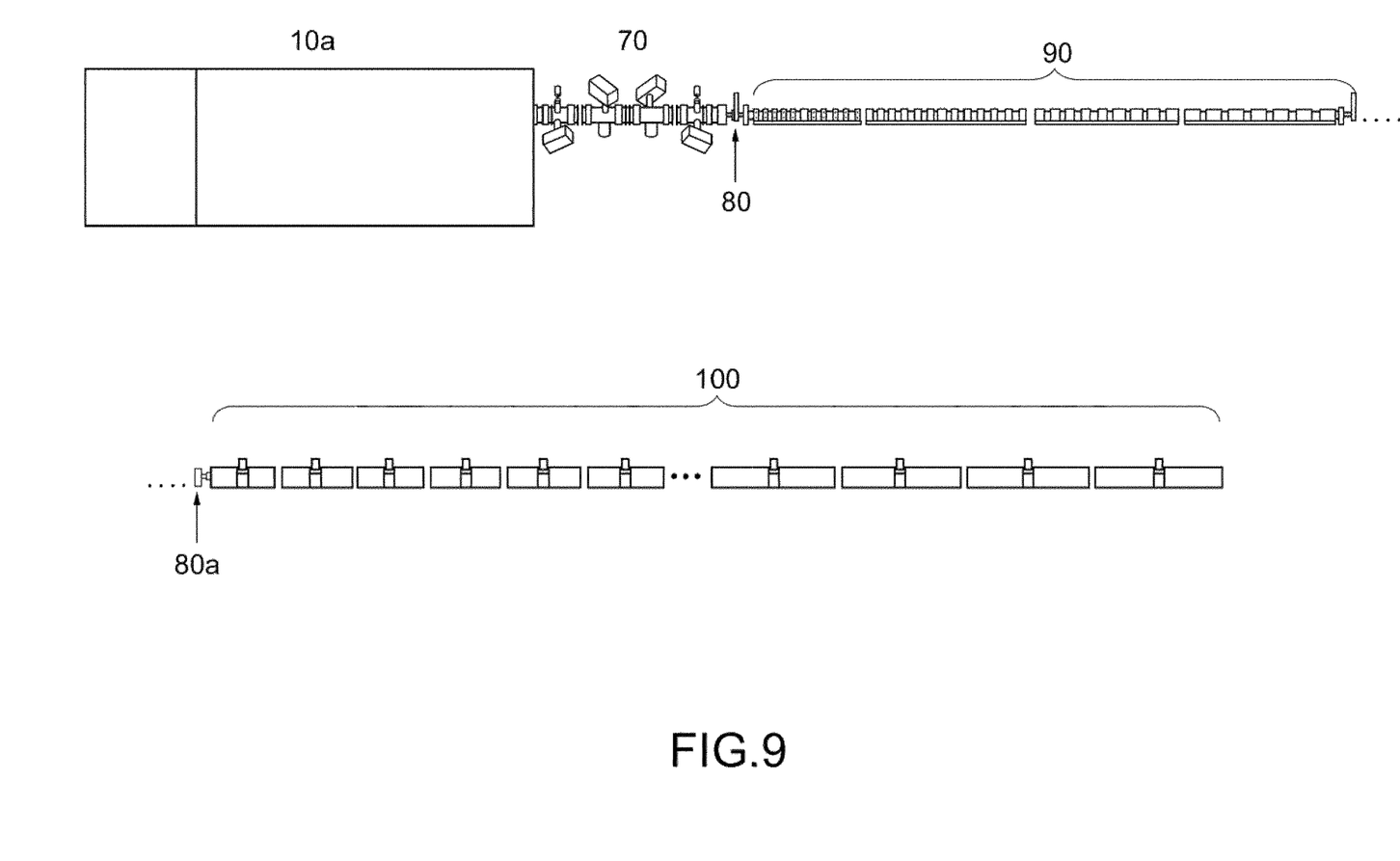
FIG. 9 shows a particular embodiment of a treatment linear accelerator which may use the invention.

FIG. 9 shows a particular embodiment of a treatment linear accelerator (split into two parts for ease of representation on the page) which comprises a proton injector assembly (10a), which comprises a proton source and pulse shaping components such as a chopper assembly, coupled to a pre-accelerator stage, for example a radiofrequency quadrupole (70) which is coupled via a medium energy beam transfer line (MBTL) (80) to a first set of linear accelerator stages comprising SCDTLs (90). In this particular embodiment there are 4 SCDTL stages but there may be more or less. The output of the last SCDTL stage is connected via a second medium energy beam transfer line (MBTL) (80a) to a second set of linear accelerator stages comprising CCLs (90). The number of CCLs in any particular machine depends on the desired maximum output energy.

Figure 10:
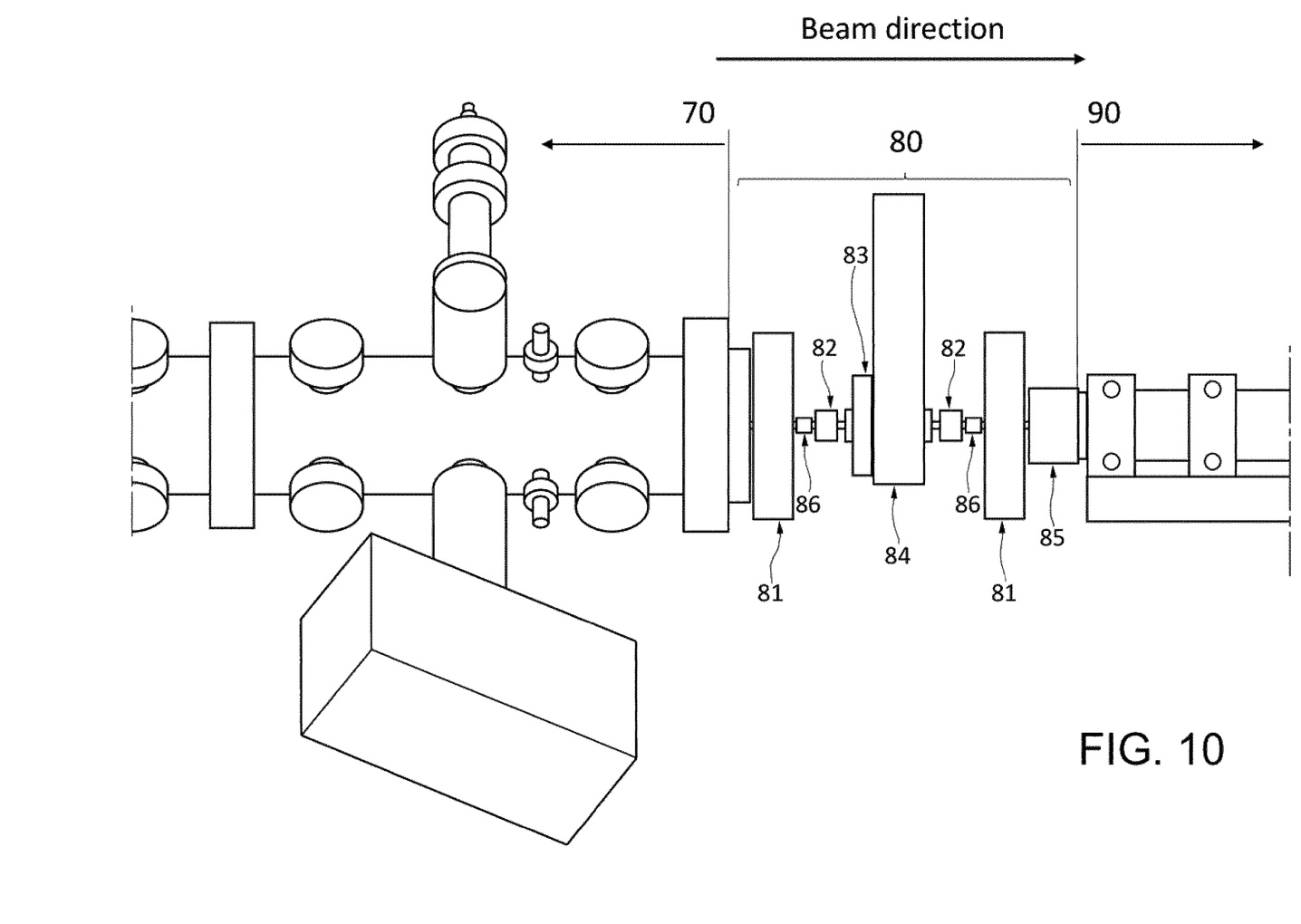
FIG. 10 shows a particular embodiment of a medium energy transfer line which may be used to form the invention.

FIG. 10 shows a particular embodiment of a medium energy transfer line which can be used to form the invention. A radiofrequency quadrupole (70) brings the pulses accelerated to 5 MeV and introduces them to a medium energy beam transfer line (MEBT) (80) which comprises:
  a steerer magnet (81), used to change direction of the beam, typically arranged to act on the beam in both a nominal x-direction and an orthogonal y-direction;
  a permanent magnet quadrupole (PMQ) (82), arranged to focus or defocus the beam;
  an AC current transformer (ACCT) or slow beam current transformer (83), used to measure transmission along the RFQ;
  a vacuum sector valve (84), to assist in creation and maintenance of the vacuum along the beam line; and this is followed by
  a further permanent magnet quadrupole (PMQ) (82); then
  a second steerer magnet (81), used to change direction of the beam, typically arranged to act on the beam in both a nominal x-direction and an orthogonal y-direction; and finally
  a beam position monitor (BPM) (85), used to measure beam position for calibration of the beam so that it correctly enters the next linear accelerator stage.

As previously described the BPM can be used as the first sensor 41 of an average current detector.

FIG. 10 also depicts bellows (86) which, as is known in the art, are a purely mechanical component (i.e. with no physics functionality, that is no electromagnetic or vacuum functionality) used to move and position components. Without bellows, all components would be "fixed" to each other and immoveable. In a particular embodiment the bellows (86) allow the PMQs to be positioned in a correct manner.

In a particular embodiment only one BPM is used as detector.

In a further typical embodiment the steerers are set using the output of the BPM, which setting may be performed automatically or through an operator.

Figure 11:
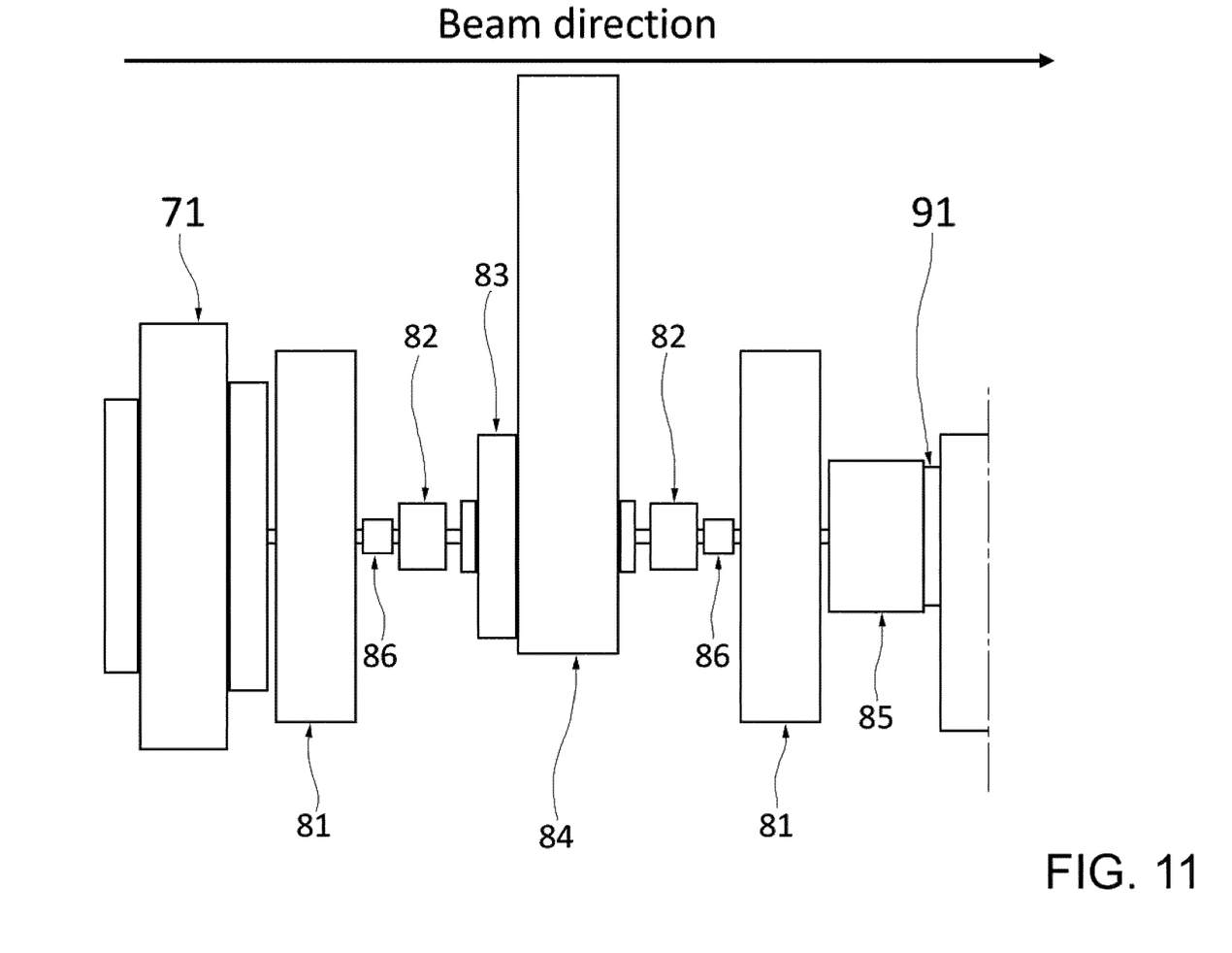
FIG. 11 shows a particular embodiment of a measuring arrangement in a medium energy transfer line which may be used to form the invention.

FIG. 11 shows a particular embodiment of a measuring arrangement in a medium energy transfer line. FIG. 11 is similar to FIG. 10 and shows similar components however in addition it shows the position of a flange (71), the RFQ output flange, which connects the RFQ to the MEBT, and the position of a further flange (91), the SCDTL input flange, which connects the MEBT to the SCDTL. The flanges assist in maintaining the vacuum in the MEBT. Following transfer through the MEBT the proton pulses move into the first SCDTL via the SCDTL input flange (91).

REFERENCES 10 proton source
10a proton injector assembly
20 linear accelerator string
21 first linear accelerator component
22 second linear accelerator component
30 pre-accelerator, buncher, stage
40 average current detector
41 first sensor
42 second sensor
43 third sensor
51 electrode
52 junction
53 amplifier
54 mixer
55 RF power detector
60 interlock
70 radiofrequency quadrupole (RFQ)
71 RFQ output flange
80 medium energy beam transfer line
80a second medium energy beam transfer line
81 steerer magnet
82 permanent magnet quadrupole (PMQ)
83 ACCT
84 vacuum sector valve
85 beam position monitor (BPM)
86 bellows
90 Side Coupled Drift Tube Linac (SCDTL)
91 SCDTL input flange
100 Coupled Cavity Linac (CCL)

The invention claimed is:

1. A linear accelerator system comprising
a source arranged to produce a pulsed beam of charged particles,
a linear accelerator string arranged to accelerate the pulsed beam up to a predetermined range of energies, and
a pre-acceleration stage interposed between the source and the linear accelerator string and arranged to accelerate the pulsed beam up to an energy suitable for beam insertion into the linear accelerator string and perform bunching of the pulsed beam,
characterized in that an average current detector is arranged to measure an average current in the pulsed beam, said average current detector comprising at least one non-interceptive sensor placed at an input side of the linear accelerator string, downstream of the pre-acceleration stage, said sensor being responsive to the pulsed beam passing thereby.

2. A system according to claim 1, further comprising an interlock device, wherein the average current detector is configured to
provide a value of the measured average current in the pulsed beam,
compare said value with an average current threshold, and
if said value exceeds the average current threshold, control the interlock device to turn off the pulsed beam.

3. A system according to claim 1, wherein the average current detector comprises at least one further sensor, hereinafter second sensor, placed downstream of said sensor, hereinafter first sensor, along said linear accelerator string, and wherein the average current detector is configured to provide a value of difference between the average current measured at the first sensor and the average current measured at the second sensor.

4. A system according to claim 3, further comprising an interlock device, wherein the average current detector is configured to
compare said difference value with a current difference threshold, and
if said difference value exceeds the current difference threshold, control the interlock device to turn off the pulsed beam.

5. A system according to claim 1, wherein said sensor is a sensor responsive to an electromagnetic field of the pulsed beam passing thereby.

6. A system according to claim 5, wherein said sensor includes a Beam Position Monitor comprising four electrodes arranged at different angular locations around a beam axis, and wherein the average current detector is configured to sum respective signals provided by the electrodes to obtain the measured average current in the pulsed beam.

7. A system according to claim 1, wherein the pre-acceleration stage is a RadioFrequency Quadrupole.

8. A system according to claim 1, wherein the linear accelerator string comprises a Side Coupled Drift Tube Linear accelerator at its input side.

9. A system according to claim 1, arranged to produce and accelerate a pulsed beam of protons.

10. A radiotherapy apparatus comprising at least one linear accelerator system according to claim 1.

11. A method of operating linear accelerator system comprising a source, a pre-acceleration stage and a linear accelerator string, said method comprising the steps of
producing a pulsed beam of charged particles,
accelerating the pulsed beam up to an energy suitable for beam insertion into the linear accelerator string and perform bunching of the pulsed beam, and
in the linear accelerator string, accelerating the pulsed beam up to a predetermined range of energies,
said method being characterized by further comprising measuring an average current in the pulsed beam by means of at least one non-interceptive sensor placed at an input side of the linear accelerator string, downstream of the pre-acceleration stage, said sensor being responsive to the pulsed beam passing thereby.

12. A method according to claim 11, further comprising providing a value of the measured average current in the pulsed beam, comparing said value with an average current threshold, and if said value exceeds the average current threshold, control an interlock device to turn off the pulsed beam.

13. A method according to claim 11, wherein said sensor is a sensor responsive to an electromagnetic field of the pulsed beam passing thereby.

14. A method according to claim 13, wherein said sensor includes a Beam Position Monitor comprising four electrodes arranged at different angular locations around a beam axis, and wherein measuring average current in the pulsed beam comprises summing respective signals provided by the electrodes to obtain the measured average current in the pulsed beam.

* * * * *